United States Patent [19]

Mair et al.

[11] Patent Number: 4,810,401

[45] Date of Patent: Mar. 7, 1989

[54] SUPERPARAMAGNETIC SOLID PARTICLES

[75] Inventors: Gunther Mair, Mannheim; Werner Steck, Ludwigshafen, both of Fed. Rep. of Germany

[73] Assignee: BASF Aktiengesellschaft, Ludwigshafen, Fed. Rep. of Germany

[21] Appl. No.: 55,066

[22] Filed: May 28, 1987

[30] Foreign Application Priority Data

Jun. 12, 1986 [DE] Fed. Rep. of Germany ....... 3619746

[51] Int. Cl.$^4$ .............................................. C04B 35/26
[52] U.S. Cl. .............................. 252/62.56; 252/62.62; 423/593; 423/594; 423/599
[58] Field of Search .................. 423/593, 594, 599; 252/62.51, 62.56, 62.62

[56] References Cited

U.S. PATENT DOCUMENTS

| | | | |
|---|---|---|---|
| 3,531,413 | 9/1970 | Rosenweig | 252/62.62 |
| 3,843,540 | 10/1974 | Reimers et al. | 252/62.52 |
| 4,096,080 | 6/1978 | Mollard et al. | 252/62.56 |
| 4,169,028 | 9/1979 | Yokoyama et al. | 252/62.56 |
| 4,238,342 | 12/1980 | Im et al. | 252/62.61 |
| 4,297,395 | 10/1981 | Buxbaum et al. | 252/62.56 |
| 4,360,441 | 11/1982 | Borrelli et al. | 252/62.59 |
| 4,425,250 | 1/1984 | Hibst | 252/62.61 |
| 4,430,239 | 2/1984 | Wyman | 252/62.51 |
| 4,485,024 | 11/1984 | Furumura et al. | 252/62.51 |
| 4,486,401 | 12/1984 | Arons et al. | 423/594 |
| 4,543,197 | 9/1985 | Karasawa et al. | 252/62.56 |
| 4,568,993 | 2/1986 | Stoppels et al. | 252/62.62 |
| 4,719,148 | 1/1988 | Stoppels et al. | 252/62.62 |

OTHER PUBLICATIONS

C. P. Bean & J. D. Livingston, "Superparamagnetism" Journal of Applied Physics, Suppl. to vol. 30, No. 4, pp. 1205–1295, 1959.
R. Brdicka, "Grundlagen der Physikalischen Chemie," 7. Auflage, Veb-Verlag, Berlin, 1968, pp. 546–549.
R. S. Tebble & D. J. Craik, "Magnetic Materials" Wiley-Interscience, London, pp. 252–270, 1969.

*Primary Examiner*—Anthony McFarlane
*Attorney, Agent, or Firm*—Keil & Weinkauf

[57] ABSTRACT

Superparamagnetic solid particles of the general formula I $$M_v Mn_w Zn_x Fe_y O_z \qquad (I)$$

where M is Co and/or Ni, v and w are each from 0 to 0.998, x is from 0.001 to 0.998, y is from 2.001 to 2.998, z is from 3.001 to 4, v+w+x is from 0.002 to 0.999, v+w+x+y is 3, v≠0 if w=0 and w≠0 or v=0, polar and nonpolar superparamagnetic liquids which contain the surfactant-coated superparamagnetic solid particles I in the form of a colloidal dispersion in polar or nonpolar liquid media, and processes for the preparation of polar and nonpolar superparamagnetic liquids.

4 Claims, No Drawings

SUPERPARAMAGNETIC SOLID PARTICLES

The present invention relates to novel superparamagnetic solid particles of the general formula I $$M_v Mn_w Zn_x Fe_y O_z \quad (I)$$

where M is Co and/or Ni, v and w are each from 0 to 0.998, x is from 0.001 to 0.998, y is from 2.001 to 2.998, z is from 3.001 to 4, v+w+x is from 0.002 to 0.999, v+w+x+y is 3, v≠0 if w=0, and w≠0 if v=0.

The present invention furthermore relates to polar and nonpolar superparamagnetic liquids which contain surfactant-coated superparamagnetic solid particles I in the form of a colloidal dispersion in liquid media.

The present invention furthermore relates to a novel improved process for the preparation of nonpolar superparamagnetic liquids from superparamagnetic solid particles, coated with anionic surfactants, and nonpolar liquid media.

The present invention also relates to a novel, improved process for the preparation of polar superparamagnetic liquids from superparamagnetic solid particles I, coated with acidic phosphates, and polar liquid media.

Superparamagnetism is understood as meaning the ideal magnetically soft behavior of a ferromagnetic or paramagnetic solid particle. Such behavior is exhibited when the magnetic energy K×V of a solid particle (K=anisotropy constant, V=particle volume) decreases continuously and at some point reaches the order of magnitude of the thermal energy k×T (k=Boltzmann constant, T=absolute temperature in Kelvin), so that there is no longer any permanent dipole. For cubic ferrites (the solid particles I according to the invention belong to this class of compounds), the critical maximum particle diameter from which this behavior is exhibited is about 5–15 nm (cf. C. P. Bean and J. D. Livingston, Superparamagnetism, J. Appl. Phys., Supplement to Volume 30, No. 4, pages 120S–129S, 1959). In the case of the cubic ferrites, assuming that they are present as monodisperse, substantially pore-free spherical particles, this critical particle diameter roughly corresponds to a BET surface area of from 40 to 130 m²/g, determined according to Brunauer, Emmet and Teller (cf. R. Brdicka, Grundlagen der Physikalischen Chemie, 7th edition, VEB-Verlag, Berlin, 1968, pages 546–549).

Superparamagnetic liquids are surfactant-stabilized colloidal dispersions of superparamagnetic solid particles in polar or nonpolar liquid media. In general, the surfactants cover the surface of the superparamagnetic solid particles in the form of a predominantly monomolecular layer and thus prevent sedimentation of the superparamagnetic solid particles in a gravity field, magnetic field and/or electric field.

Since neither coating with a surfactant nor dispersing the coated solid particles in liquid media to give a colloidal dispersion adversely affects the superparamagnetism of the original solid particles, colloidal dispersions exhibit superparamagnetic behavior, ie. hysteresis-free reversible magnetization and demagnetization behavior.

For the purposes of the present invention, the term liquid medium denotes the liquid components of a colloidal dispersion of surfactant-coated superparamagnetic solid particles, the said components being mixed with one another to give a molecular-disperse mixture; a liquid medium of this type mainly contains one or more polar or nonpolar liquids, such as water, hydrocarbons or oils, and may furthermore contain additives, such as acids, bases, salts, gases or surfactants, in molecular disperse solution. The term polar expresses the fact that the relevant liquids and liquid media are capable of undergoing dipole-dipole, dipole-ion and/or ion-ion interactions with one another or with additives, whereas the term nonpolar indicates that the relevant liquids and liquid media are incapable of such interactions.

For the sake of brevity, superparamagnetic liquids based on nonpolar liquid media will be referred to below as nonpolar superparamagnetic liquids, and those based on polar liquid media will be referred to below as polar superparamagnetic liquids.

For the purposes of the present invention, agglomerated superparamagnetic solid particles capable of sedimentation and magnetic solid particles capable of sedimentation will be referred to collectively as solid particles capable of sedimentation.

US-A-3 843 540 discloses a process for the preparation of superparamagnetic liquids from superparamagnetic solid particles and nonpolar liquid media, in which the particles are precipitated from aqueous metal salt solution, which have the chemical composition of the particles, by means of a base, coated with surfactants, transferred to nonpolar liquids, flocculated in these liquids by means of acetone, separated off, washed with acetone and then redispersed in a nonpolar liquid.

The known process does not comprise flocculation of the particles in their dispersions in polar or nonpolar liquid media by means of methanol or washing of dispersions based on nonpolar liquid media with bases and water.

US-A-4 430 239 discloses a process for the preparation of superparamagnetic liquids from superparamagnetic magnetite particles and polar liquid media, in which the particles are precipitated from aqueous metal salt solutions by means of a base, dispersed in water, coated with an acidic phosphate, flocculated with acetone, separated off and then redispersed in a polar liquid.

The known process does not comprise the use of superparamagnetic solid particles I and the use of a polar liquid 1 which boils at a lower temperature than the main component of the polar liquid medium of the superparamagnetic liquids, the polar liquid 2.

The known processes have the disadvantage that they give nonpolar or polar superparamagnetic liquids having an unacceptable content of solid particles capable of sedimentation, with the result that the saturation magnetization $M_s$ of the liquids is lower than would be expected from the amount of starting material. Moreover, such superparamagnetic liquids have unsatisfactory stability, ie. irreversible processes take place in them in the course of time, leading to the formation of further solid particles capable of sedimentation, with the result that such superparamagnetic liquids can be used only to a considerably restricted extent, if at all. Although the formation of solid particles capable of sedimentation can be suppressed to a small extent by using an excess of surfactants which is well beyond the amount required for coating the superparamagnetic solid particles, it is known (cf. US-A-3 843 540) that this increases the viscosity of the superparamagnetic liquids in an undesirable manner.

US-A-3 351 413 discloses that, in addition to cubic ferrites, magnetite and $\gamma$-Fe$_2$O$_3$ and any other solid magnetic material which can be comminuted in a suitable manner, cubic manganese zinc ferrites in general are also suitable for the preparation of superparamagnetic solid particles and superparamagnetic liquids. However, the Patent does not state that required composition, particle size and saturation magnetization $M_s$ of suitable manganese zinc ferrites.

According to US-A-4 430 239, in addition to magnetite, other ferrites too are suitable for the preparation of polar superparamagnetic liquids. However, the required composition of these ferrites is not stated.

Usually, however, superparamagnetic magnetite or $\gamma$-ferrite or superparamagnetic mixed crystals of these two cubic ferrites are used for the preparation of superparamagnetic liquids (cf. US-A-3 843 540), it being generally known that the saturation magnetization $M_s$ can be improved to a small extent, compared with the pure ferrites, by mixed crystal formation.

R.S. Tebble and D. J. Craik, Magnetic Mateials, Wiley Interscience, London, pages 252–270, 1969, have disclosed the saturation magnetization $M_s$ of nonsuperparamagnetic magnetite, MnFe$_2$O$_4$, CoFe$_2$O$_4$ and NiFe$_2$O$_4$ solid particles (cf. in particular page 256, FIG. 7.2). It is also evident, particularly from page 266, FIG. 7.10, that the saturation magnetization $M_s$ of such cubic ferrites can be increased by replacing some of the manganese, cobalt or nickel ions by zinc ions. A maximum saturation magnetization $M_s$ is achieved with a compositon of the general formula II $$M^1_w Zn_x Fe_2 O_4 \qquad \text{II}$$

where $M^1$ is Co, Ni or Mn, w is from 0.4 to 0.5, x is from 0.5 to 0.6 and w+x is 1.

However, superparamagnetic ferrites of known composition have the disadvantage that their saturation magnetization $M_s$ is comparatively low. Accordingly, large amounts of ferrites have to be used for the preparation of superparamagnetic liquids having a high saturation magnetization $M_s$. Because they inevitably have a high solids content, the relevant superparamagnetic liquids in this case have an undesirably high viscosity and are frequently unstable and hence suitable only to a limited extent for many applications.

It is an object of the present invention to provide novel superparamagnetic solid particles and liquids having improved performance characteristics, and a novel improved process for the preparation of such superparamagnetic liquids.

We have found that this object is achieved by the superparamagnetic solid particles I defined at the outset.

We have furthermore found superparamagnetic liquids which contain surfactant-coated superparamagnetic solid particles I in the form of a colloidal dispersion in liquid media.

We have also found a process for the preparation of nonpolar superparamagnetic liquids from superparamagnetic solid particles and nonpolar liquid media, in which the particles are precipitated from aqueous metal salt solutions, which have the chemical compositions of the particles, by means of a base, coated with anionic surfactants and transferred to a nonpolar liquid, wherein (a) the coated particles present in the aqueous medium are flocculated with methanol, separated off and redispersed in a nonpolar liquid and/or (b) the coated particles which have already been dispersed in any desired manner in a nonpolar liquid medium are flocculated with methanol, separated off and redispersed in a nonpolar liquid.

In a preferred embodiment of the novel process, step b is repeated twice or several times.

In another preferred embodiment, the dispersions obtained in the manner according to the invention are washed first with an aqueous base and then with water until the wash water is neutral and anions are therefore no longer detectable.

We have furthermore found a process for the preparation of polar superparamagnetic liquids from superparamagnetic solid particles and polar liquid media, in which the particles are precipitated from aqueous metal salt solutions, which have the chemical composition of the particles, by means of a base, coated with acidic phosphates and transferred from the aqueous medium to a polar liquid which has a higher boiling point than water, wherein (a') the coated superparamagnetic solid particles are transferred to a polar liquid 1 which boils at from 110° to 250° C., and (b') after the water has been separated off, a polar liquid 2 which has a higher boiling point than the liquid 1 is added to the resulting dispersion, after which the liquid 1 is removed from the dispersion.

The novel superparamagnetic solid particles I belong to the primary class of compounds comprising the cubic ferrites. Accordingly, they may be regarded as superparamagnetic modified cubic ferrites and in particular as superparamagnetic modified cubic zinc iron ferrites, whose saturation magnetization $M_s$ has been increased by modification, ie. by incorporation of cobalt, nickel and/or manganese ions into the ferrite lattice. The novel superparamagnetic solid particles I may therefore be regarded as cubic cobalt zinc iron ferrites Ia,
nickel zinc iron ferrites Ib,
cobalt nickel zinc iron ferrites Ic,
manganese zinc iron ferrites Id,
cobalt manganese zinc iron ferrites Ie,
nickel manganese zinc iron ferrites If and
cobalt nickel manganese zinc iron ferrites Ig.

Examples of novel superparamagnetic solid particles I where w=0 are:

(Ia) superparamagnetic cubic cobalt zinc iron ferrites, such as
Co$_{0.5}$Zn$_{0.2}$Fe$_{2.3}$O$_{3.7}$ or
Co$_{0.3}$Zn$_{0.1}$Fe$_{2.6}$O$_{3.84}$;

(Ib) superparamagnetic cubic nickel zinc iron ferrites, such as
Ni$_{0.4}$Zn$_{0.3}$Fe$_{2.2l}$O$_{3.5}$,
Ni$_{0.01}$Zn$_{0.05}$Fe$_{2.94}$O$_{3.95}$ or
Ni$_{0.5}$Zn$_{0.1}$Fe$_{2.4}$O$_{3.8}$;

and (Ic) superparamagnetic cubic cobalt nickel zinc iron ferrites, such as
Co$_{0.1}$Ni$_{0.3}$Zn$_{0.4}$Fe$_{2.2}$O$_4$,
Co$_{0.3}$Ni$_{0.01}$Zn$_{0.27}$Fe$_{2.42}$O$_{3.6}$ or
Co$_{0.1}$Ni$_{0.1}$Zn$_{0.7}$Fe$_{2.1}$O$_{3.9}$.

Examples of novel superparamagnetic solid particles I where v=0 are:

(Id) superparamagnetic cubic manganese zinc iron ferrites, such as $Mn_{0.5}Zn_{0.2}Fe_{2.3}O_{3.9}$,
$Mn_{0.2}Zn_{0.3}Fe_{2.5}O_{3.95}$,
$Mn_{0.1}Zn_{0.1}Fe_{2.8}O_4$ or
$Mn_{0.02}Zn_{0.05}Fe_{2.93}O_{3.8}$.

Examples of novel superparamagnetic solid particles I where $v \neq 0$ and $w \neq 0$ (which result directly from the conditions for the variables according to claim 1) are (Ie) superparamagnetic cubic cobalt manganese zinc iron ferrites, such as $Co_{0.1}Mn_{0.1}Zn_{0.35}Fe_{2.45}O_{3.9}$ or
$Co_{0.6}Mn_{0.1}Zn_{0.2}Fe_{2.1}O_4$;

(If) superparamagnetic cubic nickel manganese zinc iron ferrites, such as $Ni_{0.3}Mn_{0.1}Zn_{0.1}Fe_{2.5}O_{3.8}$ or
$Ni_{0.01}Mn_{0.01}Zn_{0.2}Fe_{2.78}O_4$;

and (Ig) superparamagnetic cubic cobalt nickel manganese zinc iron ferrites, such as $Co_{0.1}Ni_{0.15}Mn_{0.2}Zn_{0.1}Fe_{2.45}O_{3.9}$, $Co_{0.01}Ni_{0.22}Mn_{0.01}Zn_{0.002}Fe_{2.958}O_4$ or
$Co_{0.34}Ni_{0.2}Mn_{0.31}Zn_{0.1}Fe_{2.05}O_{3.72}$.

Among these novel superparamagnetic solid particles Ia to Ig, the superparamagnetic cubic cobalt manganese zinc iron ferrites Ie and the superparamagnetic cubic nickel manganese zinc iron ferrites If are particularly preferred.

The particle size of the solid particles I corresponds to a BET inner surface area of from 40 to 130, preferably from 50 to 120, in particular from 60 to 110, $m^2/g$.

In a magnetic field of 160 kA/m, the solid particles I have a saturation magnetization $M_s$ of more than 60 $nTm^3/g$.

The novel superparamagnetic solid particles I can be obtained by any suitable methods, for example by comminution of larger, nonsuperparamagnetic solid particles of appropriate composition. Advantageously, however, they are prepared by rapid precipitation from aqueous solutions in which the cobalt, nickel, and/or manganese salts and the zinc and iron salts are present in the appropriate combinations and molar ratios, with the addition of about stoichiometric amounts of aqueous bases, such as sodium hydroxide solution. The precipitation is usually carried out under an inert gas. It is advantageous if the ratio q of the content of divalent iron to the total iron content in the aqueous solutions before precipitation is from 0.01 to 0.9, preferably from 0.15 to 0.6, in particular from 0.2 to 0.5.

After the precipitation, the reaction mixture consisting of solid particles I and an aqueous medium is brought to a pH of from 10 to 12, preferably 11, in a conventional manner, after which the reaction mixture is left to stand at room temperature for a certain time and then neutralized. The solid particles I are then separated off in a conventional manner, washed and dried.

The solid particles I are very useful as components of magnetic toners and inks. However, they are particularly suitable as superparamagnetic components in the novel superparamagnetic liquids.

The superparamagnetic liquids according to the invention contain the surfactant-coated novel superparamagnetic solid particles I in the form of a colloidal dispersion in liquid media.

The liquid media may be both polar and nonpolar media, the polar media mainly containing polar liquids, and the nonpolar media mainly containing nonpolar liquids.

A suitable polar liquid is water.

Examples of suitable polar liquids which have a higher boiling point than water are ethers, such as diethylene glycol dimethyl ether, diethylene glycol diethyl ether or diethylene glycol monomethyl ether; $C_2$-$C_6$-alkyl esters of $C_1$-$C_6$-alkanemonocarboxyl acids, such as hexyl acetate, cyclohexyl acetate, pentyl propionate, ethyl butyrate, methyl pentanecarboxylate, ethyl pentanecarboxylate or methyl hexanecarboxylate; and $C_5$- and $C_6$-dialkyl esters of $C_1$-$C_7$-alkanedicarboxylic acids, such as dihexyl malonate, dihexyl succinate, dipentyl glutarate, di-n-butyl adipate, di-n-butyl pimelate, di-n-propyl hexanedicarboxylate or diethyl azelaate (diethyl heptanedicarboxylate). Polar liquids of this type boil at from 110° to 250° C. They are suitable as polar liquids 1. Hexyl acetate and cyclohexyl acetate are advantageous.

Examples of other suitable polar liquids which boil at a higher temperature than the liquids stated above are higher dialkyl esters of alkanedicarboxylic acids, such as dinonyl adipate, didecyl adipate, diisodecyl adipate, n-octyl hexanedicarboxylate, di-(2-ethylhexyl) azelaate or di-n-octyl azelaate; higher dialkyl esters of phthalic acid, isophthalic acid or terephthalic acid, such as dinonyl phthalate, didecyl phthalate, diisodecyl phthalate, undecyl phthalate, diisodecyl isophthalate or di-(2-ethylhexyl) terephthalate; higher trialkyl esters of trimellitic acid, such as tri-n-octyl trimellitate, and alkylbenzyl esters of phthalic acid, such as n-octylbenzyl phthalate. Polar liquids of this type generally boil at above 250° C. They are suitable as polar liquids 2. Diisodecyl phthalate, dinonyl adipate and diisodecyl adipate are advantageous.

Examples of suitable nonpolar liquids are aliphatic hydrocarbons, such as hexanes, heptanes, octanes, nonanes, cyclopentane, alkylcyclopentanes, cyclohexane, alkylcyclohexanes and petroleum ether having a boiling range of from 20° to 160° C.; aromatic hydrocarbons, such as benzene or toluene, and aliphatic halohydrocarbons, such as methylene chloride, chloroform, dichlorodifluoromethane or the dichlorotetrafluoroethanes. The petroleum ethers are particularly advantageous.

Other examples of suitable nonpolar liquids are mineral oils, silicone oils, oils based on fluorinated ethers, on aliphatic fluorohydrocarbons, on alkyl esters of mono- and/or dicarboxylic acis, on hydrogenated poly-α-olefins, on polyisobutylene, on alkylaromatics, on hydrogenated poly-α-olefins and alkylaromatics or on mixtures of such oils, the oils based on hydrogenated poly-α-olefins and/or on alkylaromatics, and oils based on polyisobutylene and the aliphatic mineral oils, being particularly advantageous.

The viscosity of suitable oils is in general from 2 to 1000 mPa.s at, for example, 20° C. and/or from 1 to 300 mPa.s. at, for example, 40° C. In general, their rate of evaporation at 80° C. is less than $10^{-5}$, preferably $10^{-7}$, in particular $10^{-8}$, $gcm^{-2}s^{-1}$. Many of them have a density of from 0.7 to 0.9 $gcm^{-3}$ at 20° C. Their boiling range is preferably from 200° to 600° C. under atmospheric pressure, and may be from 100° to 300° C. under from 0.01 to 0.3 mbar.

Water-soluble cationic and anionic surfactants or electrically neutral surfactants, such as ethylene oxide/propylene oxide block copolymers, are particularly suitable for coating the solid particles I; the anionic surfactants are preferred.

Accordingly, examples of suitable anionic surfactants are alkylsulfonates and their salts, for example sodium eicosanylsulfonate or potassium perfluorooctadecylsulfonate; fatty alcohol ether sulfates and their salts, such as sodium 3,6-dioxaoctadecylsulfate; monoesters of fatty alcohols with phosphoric acid and the mono- and dialkali metal salts of these esters, for example sodium and disodium octadecylphosphate; 2-ethylhexyl phosphate, di-n-octyl phosphate or oleyl phosphate; monoesters and diesters of phosphoric acid with oxyalkylated alcohols of the general formula III

where $R^1$ is $C_6$–$C_{18}$-alkyl or $C_{10}$–$C_{20}$-aralkyl, $R^2$ is $C_2$–$C_4$-alkanediyl and p is from 1 to 15, such as monoesters and diesters of phosphoric acid with oxyethylated n-octyl alcohol, oxyethylated nonyl alcohol, oxyethylated decyl alcohol, oxyethylated pentadecyl alcohol, oxypropylated octadecyl alcohol, oxyethylated ω-phenylnonyl alcohol, oxyethylated 2-ethylhexanol, oxypropylated 2-ethylhexanol, oxyethylated 7-(p-pentylphenyl)-heptyl alcohol or oxyethylated ω-phenyldecyl alcohol, or mixtures of such esters; or long-chain, monoolefinically or polyolefinically unsaturated fatty acids, where the alkenyl radical is of 16 to 25 carbon atoms, and their alkali metal and ammonium salts, for example oleic acid or sodium or ammonium oleate.

Oleic acid and its salts and the monoesters and diesters of phosphoric acid with oxyalkylated alcohols of the general formula III, where $R^1$ is $C_{12}$–$C_{17}$–aralkyl, $R^2$ is ethylene and p is from 1 to 5, are preferred, sodium oleate and the monoester of phosphoric acid with oxyethylated (p=from 3 to 5) ω-phenylnonyl alcohol being very particularly preferred.

The novel polar and nonpolar superparamagnetic liquids can be prepared in a suitable manner by prior art methods.

However, it is particularly advantageous to prepare the novel nonpolar superparamagnetic liquids by the novel process for the preparation of nonpolar superparamagnetic liquids, and the novel polar superparamagnetic liquids by the novel process for the preparation of polar superparamagnetic liquids.

The novel process for the preparation of nonpolar superparamagnetic liquids is moreover not restricted only to novel superparamagnetic liquids which contain the solid particles I but can also very successfully be used for the synthesis of nonpolar superparamagnetic liquids which contain other superparamagnetic solid particles.

Accordingly, this process according to the invention can be applied to all paramagnetic and ferromagnetic solids, provided that they can be prepared in aqueous media in the form of a colloidal dispersion, in a particle size of from 5 to 15 nm, by precipitation from their water-soluble salts by means of a base, and, after their preparation, are stable to aqueous media.

Examples of other suitable solids are, in particular, cubic ferrites, such as magnetite, γ-ferrite, manganese iron ferrite, cobalt iron ferrite, nickel iron ferrite, zinc iron ferrite and mixed crystals of magnetite and γ-ferrite.

Examples of nonpolar liquids which are suitable according to the invention are the abovementioned ones, of which the petroleum ethers, the oils based on hydrogenated poly-α-olefins and/or on alkylaromatics and the oils based on polyisobutylene and the aliphatic mineral oils are particularly advantageous.

Examples of anionic surfactants which are suitable according to the invention are the abovementioned ones, of which oleic acid and its salts are particularly advantageous.

The process has no special features in terms of process engineering, ie. no specially developed and adapted apparatuses as such are required to carry it out, and each of the individual process steps is based on known chemical methods.

The process according to the invention starts from the preparation of colloidal aqueous dispersions of superparamagnetic solid particles coated with anionic surfactants.

In general, this is achieved by rapid precipitation, under an inert gas, of the superparamagnetic solid particles from aqueous solution of salt mixtures of appropriate composition by means of roughly stoichiometric amounts of aqueous bases, such as sodium hydroxide solution. The particle size of the solid particles can be adjusted in the desired manner by varying the salt concentration and base concentration, the precipitation temperature and precipitation rate and the ratio q of the content of divalent iron to the total iron content in the aqueous solution before precipitation. The reaction mixture consisting of solid particles and the aqueous medium is usually brought to a pH of from 10 to 12, preferably 11, after the precipitation, and is then left to stand at room temperature for a certain time, usually from 15 to 60 minutes. The reaction mixture is then generally neutralized. The solid particles are then separated off from the aqueous medium in a conventional manner, for example by sedimentation in a magnetic field or by filtration, and are washed substantially electrolyte-free. Thereafter, aqueous solutions of one or more anionic surfactants, for example aqueous solutions of medium oleate, are added to the particles or to a suspension of the particles in water, the surfactants usually being employed in an excess beyond the amount usually required for covering the superparamagnetic solid particles with a monomolecular layer. The resulting colloidal dispersions of coated particles and aqueous media are brought to a pH of from 10 to 12, preferably 11, heated for a prolonged period, usually from 15 minutes to 3 hours, to 70°–100° C., preferably 90° C., while stirring, and, if required, then neutralized.

It is usual to carry out this step completely in the absence of atmospheric oxygen.

The coated particles present in the aqueous medium are then flocculated, in step a according to the invention, by the addition of methanol, the volume of the latter roughly corresponding to the volume of the aqueous medium. Advantageously, the methanol is used in an excess compared with the volume of the aqueous medium.

The flocculated coated particles are separated off from the polar aqueous medium, which principally contains water and methanol, in a conventional manner, for example by centrifuging and/or by sedimentation in a magnetic field, and, if necessary, are washed with fresh methanol and/or dried. Thereafter, the particles are redispersed in a nonpolar liquid; according to the invention, it is advantageous first to redisperse them in nonpolar liquids such as petroleum ethers, which boil at a lower temperature than the oils to be used according to the invention.

The coated particles redispersed in the nonpolar liquid medium are then again flocculated with methanol in step b according to the invention, the volume of methanol roughly corresponding to the volume of the nonpolar liquid medium. The methanol is advantageously used in an excess compared with the volume of the nonpolar liquid medium.

The flocculated coated particles are separated off from the nonpolar liquid medium, if necessary washed with fresh methanol and/or dried, and then redispersed in a nonpolar liquid. According to the invention, it is advantageous to redisperse the flocculated coated particles in a lower-boiling nonpolar liquid, such as petroleum ether, the volume of the nonpolar liquid roughly corresponding to the volume of the original nonpolar liquid medium.

Step b according to the invention can be repeated twice or several times.

Where step a according to the invention is dispensed with, the coated particles present in the aqueous medium are transferred to the nonpolar liquid medium in a known manner by adding a nonpolar liquid, thoroughly mixing the resulting polar and nonpolar liquid media and effecting phase separation, after which step b according to the invention must be carried out twice or several times.

The resulting dispersion of coated particles and nonpolar liquid medium can be washed first with an aqueous base, such as sodium hydroxide solution, potassium hydroxide solution or ammonia water, and then with water until the wash water is neutral and anions are no longer detectable therein, ie. conventional detection reactions for the relevant anions give negative results.

The washes with bases as well as those with water can be carried out continuously in suitable units, for example in extraction columns or countercurrent extractors, or batchwise, for example in separating funnels or stirred kettles. Each washing step is of course followed by phase separation. Where washing is carried out batchwise, it is advantageous to use a plurality of small portions of aqueous bases and water instead of one large portion.

In the process according to the invention, washing with aqueous bases and with water is essential when either of the two steps a and b is not carried out.

The superparamagnetic liquids obtained in this manner can, if necessary, also be dried in a suitable manner. An example of a suitable method is azeotropic distillation of the water from the nonpolar liquid medium after the addition of compounds which form azeotropic mixtures with water.

The particles can be transferred from the dispersion prepared by the novel process and consisting of superparamagnetic solid particles and the nonpolar liquid medium to another nonpolar liquid medium. This can be done, for example, by redispersing the flocculated coated particles, in step b according to the invention, in a nonpolar liquid other than that used prior to flocculation. The amount of the second nonpolar liquid can be chosen so that superparamagnetic liquids having the desired particle content result. However, it is preferable to add the second nonpolar liquid to the superparamagnetic liquid obtained by the novel process; it is advantageous for the second nonpolar liquid to boil at a very much higher temperature than that which forms the basis of the liquid nonpolar medium of the superparamagnetic liquid, and its amount is chosen so that the new dispersion has the desired particle content after the lower-boiling nonpolar liquid has been evaporated from the mixed medium. Particularly suitable lower-boiling nonpolar liquids here are petroleum ethers. Examples of suitable higher-boiling nonpolar liquids are the abovementioned oils.

The novel process for the preparation of polar superparamagnetic liquids is not restricted only to the preparation of novel polar superparamagnetic liquids based on the solid particles I but can also be used for the preparation of polar superparamagnetic liquids based on the known, abovementioned solid particles. The process has very particular advantages in the preparation of the novel polar superparamagnetic liquids.

Examples of acidic phosphates which are suitable according to the invention are the abovementioned monoesters and diesters of phosphoric acid, of which the monoesters of phosphoric acid with oxyethylated (p=3-5) ω-phenylnonyl alcohol are particularly advantageous.

Examples of polar liquids 1 which are suitable according to the invention are the abovementioned polar liquids which boil at from 110° to 250° C. Among these, hexyl acetate and cyclohexyl acetate are very particularly advantageous.

Examples of polar liquids 2 which are suitable according to the invention are the abovementioned polar liquids which boil at above 250° C. Diisodecyl phthalate, dinonyl adipate and diisodecyl adipate are particularly advantageous.

This process too employs no special methods, ie. no specially developed and adapted apparatuses as such are required for carrying it out, and each of the individual steps is based on known chemical methods.

The preparation of the aqueous dispersions of coated solid particles is carried out as described above in the process for the preparation of nonpolar superparamagnetic liquids, except that, instead of, for example, oleic acid, acidic phosphates are used for coating.

In contrast to this process, polar liquids 1 are then added, in step a', to the aqueous dispersion of the solid particles I coated with acidic phosphates, the volumes of the said liquids roughly corresponding to the volumes of the aqueous media.

It is also possible first to prepare the solid particles, isolate them and redisperse them in a mixture of water, acidic phosphates and polar liquids 1.

Thereafter, the temperature of the stirred dispersions is increased to 160°–180° C., and the water present therein is distilled off. The anhydrous dispersions are then stirred for a certain time, for example for 30 minutes, at from 160° to 180° C.

After cooling, the dispersions of the coated solid particles I in the polar liquids 1 are then mixed with the desired amount of polar liquids 2 in the step b'. The liquids 1 are then distilled off under reduced pressure, and polar superparamagnetic liquids result.

It is advantageous to carry out this process under an inert gas.

Furthermore, the two processes according to the invention may comprise further steps. For example, it may prove advantageous if the solid particles capable of sedimentation are separated off, after the steps according to the invention, from the resulting dispersions of coated particles and liquid media, by centrifuging and/or by sedimentation in a magnetic field, centrifuging generally being preferred.

Although, in the novel process, it is not essential to carry out centrifuging, it is nevertheless always effected since it is very useful for demonstrating the advantages of the processes according to the invention. Since the solid particles capable of sedimentation are removed from the dispersions during centrifuging, the saturation magnetization $M_s$ of dispersions having a high content of solid particles capable of sedimentation decreases compared with the saturation magnetization $M_s$ of similar dispersions having a low content of such particles. Thus, if the relevant dispersions are prepared by different processes but using the same starting materials in the same amounts, the different saturation magnetizations $M_s$ of the relevant dispersions, ie. of the superparamagnetic liquids, constitute a direct measure of the success of the different processes.

The processes according to the invention have a large number of advantages over the prior art. They can be used to prepare nonpolar and polar superparamagnetic liquids in a simple and exactly reproducible manner. The superparamagnetic liquids thus prepared have a substantially higher saturation magnetization $M_s$, higher stability and a lower viscosity than those prepared according to the prior art. The novel nonpolar and polar superparamagnetic liquids based on the solid particles I have additional advantages in terms of saturation magnetization $M_s$, stability and viscosity when they are prepared by the processes according to the invention.

In general, the polar and nonpolar superparamagnetic liquids prepared by the novel process and based on known superparamagnetic solid particles as well as the novel polar and nonpolar superparamagnetic liquids based on solid particles I, and in particular the polar and nonpolar superparamagnetic liquids based on the solid particles I and prepared by the novel process, are very suitable as shaft seals, in particular in computer and vacuum technology, for camping loudspeakers and stepping motors in the electrical industry, for gravity separation of solids such as ores or metals, particularly in mining or in the chemical industry, for the microencapsulation of active compounds, particularly in medicine or crop protection, for the elimination of oil pollution, for energy conversion generally, for liquid crystal displays, for magnetic valves, in particular in high vacuum and ultrahigh vacuum technology, as fuel additives, particularly in space technology, and for labeling techniques, particularly in medicine, biochemistry, microbiology and bioengineering.

EXAMPLES

In the Examples and Comparative Experiments, the saturation magnetization $M_s$ (nTm$^3$/g) of both the superparamagnetic solid particles and the superparamagnetic liquids was determined in a magnetic field of 160 kA/m directly after the preparation. In the case of superparamagnetic liquids which were prepared by different processes but using the same starting materials in the same amounts, and from which the solid particles capable of sedimentation were separated off by centrifuging, the saturation magnetization $M_s$ was a direct measure of the success of the particular preparation process used.

In some cases, the yield, in %, of the surfactant-coated superparamagnetic solid particles was furthermore determined by weighing the solid particles capable of sedimentation which were separated off by centrifuging, the theoretical yield being set at 100%.

The inner surface area (m$^2$/g) of isolated and dried superparamagnetic solid particles was measured by the BET method. The inner surface area served as a measure of the particle size.

The stability of the polar and nonpolar superparamagnetic liquids was determined as follows.

The superparamagnetic liquids were stored for 7 days at room temperature in vertical tubes having a height of 140 mm and a diameter of 3 mm. After this time, the induction method was used to test whether the saturation magnetization $M_s$ had formed a gradient in the vertical liquid columns. If there was a decrease in the saturation magnetization $M_s$ in the upper regions of the liquid columns and an increase in the saturation magnetization $M_s$ in the lower regions, this indicated irreversible changes, accompanied by sedimentation, in the relevant superparamagnetic liquids, ie. the relevant superparamagnetic liquids were unstable. The extent of the instability was evaluated from the function saturation magnetization $M_s = f$ (height of the point of measurement in the liquid column), measured by the induction method, and was rated as follows:

1 no sedimentation, stable
2 slight sedimentation which is just detectable
3 slight but clearly detectable sedimentation
4 pronounced sedimentation
5 virtually complete sedimentation.

The viscosity (mPa.s) of the superparamagnetic liquids was determined using a rotational viscometer.

EXAMPLES 1 TO 7

Preparation of novel superparamagnetic solid particles I; general method of preparation Metal chlorides in the desired combination and the desired molar ratio were dissolved in water. This solution was rapidly added to an initially taken, roughly stoichiometric amount of aqueous sodium hydroxide solution under an inert gas, solid particles I of the desired composition and size being formed. The reaction mixture consisting of the particles and the aqueous medium was brought to pH 11 by adding hydrochloric acid, and was then left to stand for 30 minutes at room temperature. The reaction mixture was then neutralized. The solid particles I present therein were isolated from the aqueous medium by filtration, washed several times with water and dried in the air at 120° C.

Table 1 provides information on the composition of the metal salt solutions and on that of the novel superparamagnetic solid particles I.

Table 2 summarizes the measured values determined for the solid particles I.

TABLE 1

Composition of the metal salt solutions before precipitation and composition of the novel superparamagnetic solid particles I precipitated from these solutions

| Example No. | Composition of the metal salt solutions, stated as a molar ratio of the metal ions | | | | | | $\left( q \dfrac{Fe^{2\oplus}}{Fe^{2\oplus} + Fe^{3\oplus}} \right)$ | Composition of the solid particles I |
|---|---|---|---|---|---|---|---|---|
| | $Co^{2\oplus}$ | $Ni^{2\oplus}$ | $Mn^{2\oplus}$ | $Zn^{2\oplus}$ | $Fe^{2\oplus}$ | $Fe^{3\oplus}$ | | |
| 1 | — | — | 0.5 | 0.2 | 0.8 | 1.5 | 0.38 | $Mn_{0.5}Zn_{0.2}Fe_{2.3}O_{3.9}$ |
| 2 | — | — | 0.2 | 0.3 | 0.8 | 1.7 | 0.32 | $Mn_{0.2}Zn_{0.3}Fe_{2.5}O_{3.97}$ |
| 3 | — | — | 0.1 | 0.1 | 0.8 | 2.0 | 0.28 | $Mn_{0.1}Zn_{0.1}Fe_{2.8}O_{3.8}$ |
| 4 | — | — | 0.48 | 0.12 | 1.2 | 1.2 | 0.5 | $Mn_{0.48}Zn_{0.12}Fe_{2.4}O_{3.95}$ |
| 5 | — | — | 0.2 | 0.3 | 0.5 | 2.0 | 0.2 | $Mn_{0.2}Zn_{0.3}Fe_{2.5}O_4$ |
| 6 | 0.1 | — | 0.2 | 0.2 | 0.7 | 1.8 | 0.27 | $Mn_{0.2}Co_{0.1}Zn_{0.2}Fe_{2.5}O_{3.7}$ |

TABLE 1-continued

Composition of the metal salt solutions before precipitation and composition of the novel superparamagnetic solid particles I precipitated from these solutions

| Example No. | Composition of the metal salt solutions, stated as a molar ratio of the metal ions | | | | | | $\left(q \dfrac{Fe^{2\oplus}}{Fe^{2\oplus}+Fe^{3\oplus}}\right)$ | Composition of the solid particles I |
|---|---|---|---|---|---|---|---|---|
| | $Co^{2\oplus}$: | $Ni^{2\oplus}$: | $Mn^{2\oplus}$: | $Zn^{2\oplus}$: | $Fe^{2\oplus}$: | $Fe^{3\oplus}$ | | |
| 7 | — | 0.1 | 0.2 | 0.2 | 0.7 | 1.8 | 0.27 | $Mn_{0.2}Ni_{0.1}Zn_{0.2}Fe_{2.5}O_{3.96}$ |

TABLE 2

Saturation magnetization $M_s$ and BET inner surface area of the novel solid particles I

| Example no. | Saturation magnetization $M_s$ ($nTm^3/g$) | Inner surface area ($m^2/g$) |
|---|---|---|
| 1 | 68 | 89 |
| 2 | 72 | 92 |
| 3 | 70 | 100 |
| 4 | 66 | 64 |
| 5 | 67 | 116 |
| 6 | 75 | 67 |
| 7 | 75 | 84 |

COMPARATIVE EXPERIMENT A

Preparation of prior art superparamagnetic solid particles;

method of preparation

Superparamagnetic magnetite particles ($Fe_3O_4$) were prepared by the general method described in Examples 1 to 7. The ratio q was 0.36. The superparamagnetic magnetite particles had a saturation magnetization $M_s$ of 54 $nTm^3/g$ and a BET inner surface area of 104 $m^2/g$.

COMPARATIVE EXPERIMENT B

Preparation of superparamagnetic manganese zinc iron ferrite particles whose composition corresponds to that of prior art paramagnetic particles;

method of preparation

Superparamagnetic manganese zinc iron ferrite particles were prepared by the general method described in Examples 1 to 7, the molar ratio of metal ions in the metal salt solution before precipitation being $Mn^{2\oplus}:Zn^{2\oplus}:Fe^{2\oplus}:Fe^{3\oplus}=0.5:0.5:0.6:1.4$ and q being 0.36. The superparamagnetic solid particles obtained had the composition $Mn_{0.5}Zn_{0.5}Fe_2O_4$ and were not according to the invention. This composition corresponded to that of paramagnetic manganese zinc iron ferrite particles of the prior art, for which the saturation magnetization $M_s$ is known to have a maximum value. In contrast, the superparamagnetic $Mn_{0.5}Zn_{0.5}Fe_2O_4$ solid particles had an inner surface area of 94 $m^2/g$ and a saturation magnetization $M_s$ of only 50 $nTm^3/g$, which was substantially below that of novel superparamagnetic solid particles I.

EXAMPLES 8 TO 11

Preparation of novel nonpolar superparamagnetic liquids from the novel superparamagnetic solid particles I;

general method of preparation

The moist filter cake of solid particles I which was obtained by the general method described in Examples 1 to 7 was suspended in water. A solution of sodium oleate in water was added to this suspension, the amount of sodium oleate being chosen so that it was at least sufficient for coating the solid particles I.

Petroleum ether was added to this dispersion of coated solid particles I in an aqueous medium, the number of parts by volume of petroleum ether added being not less than the number of parts by volume of aqueous medium. The resulting mixture of two liquid phases was mixed thoroughly, the surfactant-coated superparamagnetic solid particles being transferred to the petroleum ether. The mixture was then left to stand until the two liquid phases had again separated completely. The solid-free aqueous medium was then separated off and discarded.

The coated solid particles I were then flocculated twice in their dispersion in petroleum ether by adding methanol in a number of parts by volume which was not less than the number of parts by volume of petroleum ether; after separation of the petroleum ether/methanol medium, the said solid particles were redispersed each time in the same number of parts by volume of fresh petroleum ether.

A higher-boiling nonpolar liquid was then added, the number of parts by weight of this liquid corresponding to the desired content of coated solid particles I in the superparamagnetic liquid, and the petroleum ether was distilled off.

Table 3 provides information on the starting materials and the composition of the novel superparamagnetic liquids prepared.

Table 4 summarizes the measured results obtained for the said liquids.

TABLE 3

Preparation of novel superparamagnetic liquids from novel superparamagnetic solid particles I

| Example no. | Solid particles according to | Starting materials Nonpolar liquids | | Superparamagnetic liquid: % by weight of solid particles |
|---|---|---|---|---|
| | | Chemical nature | Physical properties | |
| 8 | Example 2 | alkylaromatic + hydrogenated poly-α-olefin | Density (20° C.): 0.87 $gcm^{-3}$ Viscosity (40° C.): 78 mPa.s | 32 |
| 9 | Example 2 | polyisobutylene | Density (20° C.): 0.89 $gcm^{-3}$ Viscosity (20° C.): 118 mPa.s | 31 |

TABLE 3-continued

Preparation of novel superparamagnetic liquids from novel superparamagnetic solid particles I

| Example no. | Solid particles according to | Starting materials Nonpolar liquids | | Superparamagnetic liquid: % by weight of solid particles |
|---|---|---|---|---|
| | | Chemical nature | Physical properties | |
| 10 | Example 6 | aliphatic mineral oil | Boiling range: 290–390° C. Weight average molecular weight: 320 Density (20° C.): 0.78 gcm$^{-3}$ Viscosity (25° C.): 2 mPa.s Boiling range$^a$: 204–247° C. | 37.3 |
| 11 | Example 7 | aliphatic mineral oil | Density (20° C.): 0.78 gcm$^{-3}$ Viscosity (25° C.): 2 mPa.s Boiling range$^a$: 204–247° C. | 44.6 |

$^a$: At the low temperature, 5% of the oil evaporates, and at the higher temperature 95% (under atmospheric pressure)

TABLE 4

Saturation magnetization $M_s$ and $M_s$/% by weight of solid particles I for the novel superparamagnetic liquids

| Example no. | $M_s$ (nTm$^3$/g) | $M_s$/% by weight (nTm$^3$/g. % by weight) |
|---|---|---|
| 8 | 26 | 0.81 |
| 9 | 24 | 0.77 |
| 10 | 29 | 0.78 |
| 11 | 35 | 0.78 |

EXAMPLES 12 TO 15

Preparation of novel nonpolar superparamagnetic liquids by the appropriate novel process;

method of preparation

Four solutions of 25.46 g of MnCl$_2$.4H$_2$O, 11.69 g of ZnCl$_2$, 68.2 g of FeCl$_2$.4H$_2$O and 197.06 g of FeCl$_3$.6H$_2$O, in 400 ml of water in each case, were prepared. These solutions were each added to 400 ml of 8N sodium hydroxide solution under nitrogen. The four reaction mixtures were brought to pH 11 under nitrogen by adding further sodium hydroxide solution, left to stand for 30 minutes and neutralized with hydrochloric acid. The solid particles I present in the four reaction mixtures were caused to settle out under nitrogen in a magnetic field, after which the aqueous media were decanted and the solid particles I were extracted under nitrogen with water until the wash water was neutral and anions were no longer detectable therein.

All samples had the novel composition Mn$_{0.3}$Zn$_{0.2}$Fe$_{2.5}$O$_4$.

The four samples were each suspended in 800 ml of water under nitrogen, after which solutions of 25 g of oleic acid in 500 ml of sodium hydroxide solution (pH 11) were added to these suspensions. The resulting mixtures were brought to pH 11 under nitrogen, stirred at 80° C. for 30 minutes and then cooled to room temperature.

The coated solid particles I were flocculated in the resulting dispersions by adding 1500 ml of methanol in each case, separated off from the water/methanol media, washed with methanol, dried, and redispersed in 1500 ml of petroleum ether in each case.

The coated solid particles I were flocculated in the resulting dispersions by adding 3000 ml of methanol in each case, separated off from the petroleum ether/methanol media, dried, and redispersed in 1500 ml of petroleum ether in each case.

The solid particles capable of sedimentation were removed from these four dispersions by centrifuging.

318.33 g of a higher-boiling nonpolar liquid were added to each of these four dispersions, the amount of the said liquid being based in each case on a theoretical solids content of 30% by weight for the superparamagnetic liquids freed from the petroleum ether.

The petroleum ether was then removed from the dispersions by evaporation under reduced pressure, after which four superparamagnetic liquids based on higher-boiling nonpolar liquid media resulted. These superparamagnetic liquids were centrifuged again.

The following higher-boiling nonpolar liquids were used:

In Example 12:
An oil consisting of alkylaromatics and hydrogenated poly-α-olefins; physical properties: density (20° C.) 0.86 gcm$^{-3}$, viscosity (40° C.) 28 mPa.s;

in Example 13:
A hydrogenated poly-α-olefin oil; physical properties:
density (20° C.) 0.82 gcm$^{-3}$, viscosity (40° C.) 15 mPa.s;

in Example 14:
A monoalkylbenzene; physical properties: boiling range around 120° C. at 0.047 mbar, density (20° C.) 0.89;

in Example 15:
A polyisobutylene oil; physical properties: density (20° C.) 0.83 gcm$^{-3}$, viscosity (20° C.) 118 mPa.s, boiling range (atmospheric pressure) 290 (5% of the oil vaporizes)—390° C. (95% of the oil vaporizes), weight average molecular weight 320.

Table 5 provides information on the yield of solid particles I, the saturation magnetization $M_s$ of the novel superparamagnetic liquids and their viscosity and stability.

TABLE 5

EXAMPLES 12 TO 15, TEST RESULTS

| Example no. | Yield of solid particles I (%) | Saturation magnetization $M_s$ of the superparamagnetic liquids ($nTm^3/g$) | Viscosity (mPa.s) at 20° C. | 40° C. | 80° C. | Stability (Rating) |
|---|---|---|---|---|---|---|
| 12 | >95 | 29 | 210 | 69 | 13 | 1 |
| 13 | >95 | 29 | 76 | 33 | 11 | 1 |
| 14 | >90 | 19 | 18 | 9 | 4 | 1 |
| 15 | >95 | 26 | 38 | 17 | 6 | 1 |

EXAMPLES 16a TO 16f

Preparation of known nonpolar superparamagnetic liquids by the appropriate novel process;

method of preparation

A dispersion of superparamagnetic magnetite particles, coated with anionic surfactants, and an aqueous medium was prepared from 195 g of $FeCl_3.6H_2O$ and 103 g of $FeCl_2.4H_2O$ by the preparation method described in Examples 12 to 15.

The particular magnetite particles were flocculated in this dispersion by adding methanol (1000 ml) and were redispersed, as described above, in petroleum ether (1000 ml), flocculated again with methanol (1000 ml) and then again redispersed in petroleum ether (1000 ml).

The dispersion thus obtained was then centrifuged and divided into six equal portions.

Various higher-boiling nonpolar liquids were added to each of these portions in an amount (26.6 g) based on a theoretical solids content of 37.5% by weight for the petroleum ether-free superparamagnetic liquids, the following being used:

In Example 16a:
A polyisobutylene oil; physical properties: density (20° C.) 0.83 $gcm^{-3}$, viscosity (20° C.) 118 mPa.s, boiling range (atmospheric pressure) 290 (5% of the oil evaporates)—390° C. (95% of the oil evaporates), weight average molecular weight 320;

in Example 16b:
An alkylaromatic oil; physical properties: density (20° C.) 0.87 $gcm^{-3}$, viscosity (40° C.) 38 mPa.s;

in Example 16c:
An alkylaromatic oil; physical properties: density (20° C.) 0.86 $gcm^{-3}$, viscosity (40° C.) 37 mPa.s, boiling range (atmospheric pressure) 345 (5% of the oil evaporates)—385° C. (95% of the oil evaporates);

in Example 16d:
A monoalkylbenzene oil; physical properties: density (20° C.) 0.83 $gcm^{-3}$, boiling point 145° C. under 0.2 mbar;

in Example 16e:
A hydrogenated poly-α-olefin oil; physical properties: density (20° C.) 0.82 $gcm^{-3}$, viscosity (40° C.) 14 mPa.s;

in Example 16f:
An oil consisting of alkylaromatics and hydrogenated poly-α-olefins; physical properties: density (20° C.) 0.87 $gcm^{-3}$, viscosity (40° C.) 28 mPa.s.

The petroleum ether was removed from the resulting six dispersions by evaporation under reduced pressure, after which superparamagnetic liquids based on higher-boiling nonpolar liquid media were obtained.

These were centrifuged separately, and the total yield of superparamagnetic magnetite particles was then determined as 82.6%.

Table 6 summarizes the values determined for the saturation magnetization $M_s$ and the stability of the superparamagnetic liquids. The values of Examples 16a to 16e from Table 6 can be compared directly with the corresponding values of the Comparison Experiments Ca to Ce from Table 7, as follows: 16a with Ca, 16b with Cb, 16c with Cc, 16d with Cd and 16e with Ce.

TABLE 6

EXAMPLES 16a TO 16f, TEST RESULTS

| Example no. | Saturation magnetization $M_s$ ($nTm^3/g$) | Stability (Rating) |
|---|---|---|
| 16a | 25 | 1 |
| 16b | 30 | 2 |
| 16c | 30 | 2 |
| 16d | 23 | 2 |
| 16e | 25 | 2 |
| 16f | 29 | 2 |

COMPARATIVE EXPERIMENTS Ca TO Ce

Preparation of Known Superparamagnetic Liquids by a Prior Art Process;

Method of Preparation

A dispersion consisting of superparamagnetic magnetite particles coated with anionic surfactants and an aqueous medium was prepared by the preparation method described in Examples 16a to 16f.

The relevant magnetite particles were transferred directly from this dispersion to 1000 ml of petroleum ether by adding the petroleum ether to the aqueous dispersion, and the resulting mixture of two liquid phases was mixed vigorously. After phase separation, the aqueous medium was discarded.

The resulting dispersion of coated magnetite particles and petroleum ether was centrifuged and divided into five equal portions. 26.6 g of each of the oils stated in Examples 16a to 16e were added to each of these five portions, after which petroleum ether was removed from the portions, and the resulting superparamagnetic liquids were centrifuged separately.

The total yield of superparamagnetic magnetite particles was 72%.

Table 7 summarizes the values determined for the saturation magnetization $M_s$ and for the stability of the superparamagnetic liquids. The values of Comparative Experiments Ca to Ce from Table 7 can be compared directly with the corresponding values of Examples 16a to 16e from Table 6, as follows: Ca with 16a, Cb with 16b, Cc with 16c, Cd with 16d and Ce with 16e.

TABLE 7

COMPARATIVE EXPERIMENTS Ca TO Ce, TEST RESULTS

| Comparative Experiment | Saturation magnetization $M_s$ ($nTm^3/g$) | Stability (Rating) |
|---|---|---|
| Ca | 21 | 2 |
| Cb | 12 | 3 |
| Cc | 11 | 3 |
| Cd | 4 | 4 |
| Ce | 3 | 4 |

EXAMPLES 17 TO 21

Preparation of known nonpolar superparamagnetic liquids by the appropriate novel process;

method of preparation

Five colloidal dispersions of superparamagnetic magnetite particles, coated with anionic surfactants, in aqueous media were prepared by the preparation method described in Examples 16a to 16f.

The relevant magnetite particles were transferred from each of these aqueous dispersions to 3000 ml of Petroleum ether by the method described in Comparative Experiments Ca to Cf.

Each of the dispersions obtained after phase separation and consisting of the relevant magnetite particles and petroleum ether were washed three times with 1000 ml of sodium hydroxide solution (pH 12) in each case.

Each of these dispersions was washed with 500 ml portions of water until the wash water was neutral and chlorine ions were no longer detectable therein with silver nitrate.

Each of the five washed dispersions was centrifuged, after which 223.1 g of an oil were added to each dispersion, the stated amount being based on a theoretical solids content of 30% by weight for the superparamagnetic liquids. Removal of the petroleum ether from the colloidal dispersions gave five superparamagnetic liquids, which were centrifuged separately.

The following oils were used:

In Example 17:

A polyisobutylene oil; physical properties: density (20° C.) 0.83 gcm$^{-3}$, viscosity (20° C.), 118 mPa.s, boiling range (atmospheric pressure) 290 (5% of the oil evaporates)—390° C. (95% of the oil evaporates), weight average molecular weight 320;

in Example 18:

A mineral oil (hydrocracking oil); physical properties: density (20° C.) 0.8 gmc$^{-3}$, viscosity (40° C.) 18 mPa.s, boiling range (atmospheric pressure) 360 (5% of the oil evaporates)—520° C. (95% of the oil evaporates);

in Example 19:

A hydrogenated poly-α-olefin oil; physical properties: density (20° C.) 0.82 gcm$^{-3}$, viscosity (40° C.) 14 mPa.s;

in Example 20:

An oil consisting of alkylaromatics and hydrogenated poly-α-olefins; physical properties: density (20° C.) 0.87 gcm$^{-3}$, viscosity (40° C.) 28 mPa.s;

in Example 21:

An alkylaromatic oil; physical properties: density (20° C.) 0.87 gcm$^{-3}$, viscosity (40° C.) 87 mPa.s, boiling range (atmospheric pressure) 360 (5% of the oil evaporates)—390° C. (95% of the oil evaporates).

Table 8 summarizes the values determined for the saturation magnetization $M_s$, for the stability and for the viscosity of the superparamagnetic liquids.

The values of Examples 17 to 21 from Table 8 can be compared directly with the values of the Comparative Experiments D to H from Table 9 as follows: 17 with D, 18 with E, 19 with F, 20 with G and 21 with H.

TABLE 8

EXAMPLES 17 TO 21, TEST RESULTS

| Example no. | Saturation magnetization $M_s$ (nTm$^3$/g) | Viscosity (mPa.s) at 20° C. | 40° C. | 80° C. | Stability (Rating) |
|---|---|---|---|---|---|
| 17 | 24 | 86 | 32 | 9 | 1 |
| 18 | 8 | 34 | 16 | 6 | 1 |
| 19 | 20 | 70 | 30 | 19 | 1 |
| 20 | 23 | 214 | 67 | 14 | 1 |
| 21 | 21 | 486 | 118 | 19 | 1 |

COMPARATIVE EXPERIMENTS D to H

Preparation of known nonpolar superparamagnetic liquids by a prior art process;

method of preparation

Five dispersions of magnetite particles, coated with anionic surfactants, in petroleum ether were prepared by the preparation method described in Comparative Experiments Ca to Ce.

223.1 g of each of the oils described in Examples 17 to 21 were added directly to each of these five dispersions, after which the petroleum ether was removed from the dispersions.

The resulting superparamagnetic liquids were centrifuged separately.

Table 9 summarizes the values determined for the saturation magnetization $M_s$, for the stability and for the viscosity of the superparamagnetic liquids. The values of Comparative Experiments D to H from Table 9 can be compared directly with the values of Examples 17 to 21 from Table 8, as follows: D with 17, E with 18, F with 19, G with 20 and H with 21.

TABLE 9

COMPARATIVE EXPERIMENTS D TO H, TEST RESULTS

| Comparative Experiment | Saturation magnetization $M_s$ (nTm$^3$/g) | Viscosity (mPa.s) at 20° C. | 40° C. | 80° C. | Stability (Rating) |
|---|---|---|---|---|---|
| D | 18 | 56 | 21 | 6 | 3 |
| E | 3 | 47 | 21 | 7 | 5 |
| F | 10 | 45 | 20 | 7 | 4 |
| G | 15 | 119 | 38 | 9 | 4 |
| H | 12 | 251 | 26 | 13 | 4 |

Preparation of a known nonpolar superparamagnetic liquid by the appropriate novel process;

method of preparation

A dispersion of superparamagnetic magnetite particles, coated with anionic surfactants, in petroleum ether was prepared by the preparation method described in Examples 16a to 16f.

This dispersion was extracted three times with 250 ml of sodium hydroxide solution (pH 11), washed with 250 ml portions of water, centrifuged and mixed with 213.5 g of a polyisobutylene oil (for the physical properties, see Examples 9, 15, 16a or 17), these steps being carried out according to the preparation method described in Examples 17 to 21; this amount of oil was based on a theoretical solids content of 33% by weight for the superparamagnetic liquid.

The superparamagnetic liquid resulting after removal of the petroleum ether was again centrifuged. Thereafter, its saturation magnetization $M_s$ was determined as 21 nTm$^3$/g and its viscosity as 63 mPa.s at 20° C., 24 mPa.s at 40° C. and 7 mPa.s at 80° C. The superparamagnetic liquid was stable (rating 1).

COMPARATIVE EXPERIMENTS I and J

Experiments to prepare known nonpolar superparamagnetic liquids by prior art flocculation methods;

procedures

In Comparative Experiment I, an attempt was made to flocculate and further process a dispersion prepared and divided into portions according to the experimental method described in Examples 16a to 16f, and consisting of magnetite particles, coated with anionic surfactants, and an aqueous medium, with prior art liquids such as ethanol or acetone.

In Comparative Experiment J, an attempt was made to flocculate and further process a dispersion prepared and divided into portions according to the experimental method described in Comparative Experiments Ca to Ce, and consisting of superparamagnetic magnetite particles, coated with anionic surfactants, in petroleum ether, with prior art liquids such as ethanol or acetone.

In every case, however, the flocculated superparamagnetic magnetite particles could be redispersed in petroleum ether only to a small extent. Furthermore, this procedure gave so many solid particles capable of sedimentation that the experiments had to be terminated because the yield of superparamagnetic solid particles had become too small.

EXAMPLES 22 TO 28

Preparation of novel polar superparamagnetic liquids by the appropriate novel process;

method of preparation

Seven samples of novel solid particles I having the composition

$Mn_{0.3}Zn_{0.2}Fe_{2.5}O_4$ were each prepared from 147.1 g of $FeCl_3.6H_2O$, 68.2 g of $FeCl_2.2H_2O$, 25.5 g of $MnCl_2.4H_2O$ and 11.7 g of $ZnCl_2$ by the general preparation method described in Examples 1 to 7. The dry weight of each of the samples was 100 g.

Each of the seven samples was redispersed under nitrogen in a mixture of 200 ml of water, 20 or 30 g of the monoester of phosphoric acid with oxyethylated (p=3-5) ω-phenylnonyl alcohol and 400 ml of cyclohexyl acetate, and the desired dispersion was heated to 160° C., the water distilling off.

The resulting seven dispersions of solid particles I and the polar liquid 1 were stirred for a further 30 minutes at 160° C. After cooling, they were centrifuged in order to separate off any solid particles capable of sedimentation and to determine the yield of solid particles I in these dispersions.

Polar liquids 2 were then added, the number of parts by weight of these liquids corresponding to the desired content of solid particles I in the polar superparamagnetic liquids, and the polar liquid 1 was distilled off under reduced pressure.

No further solid particles capable of sedimentation could be removed from the resulting polar superparamagnetic liquids by centrifuging.

Table 10 provides information on the type and amount of substances used, the yield of solid particles I and the measured values obtained for the polar superparamagnetic liquids.

The Examples from Table 10 can be compared directly with those from Table 11, as follows: 22 with 29, 23 with 30, 24 with 31, 25 with 32 and 27 with 33.

The comparison shows that, with the aid of the novel solid particles I and the process according to the invention, polar superparamagnetic liquids having particularly advantageous properties are obtained.

TABLE 10

| | | | EXAMPLES 22 TO 28: SUBSTANCES AND TEST RESULTS | | | | |
|---|---|---|---|---|---|---|---|
| | | Yields of solid | Polar superparamagnetic liquid | | | | |
| | Acidic | particles I in | | | Saturation | Viscosity | |
| Example no. | phosphate (g) | the polar liquid 1 (%) | % by weight solids particles I | Polar liquid 2 | magnetization $(nTm^3/g)$ | at 20° C. (mPa.s) | Stability (Rating) |
| 22 | 20 | 70.5 | 37.5 | diisodecyl phthalate | 24 | — | 1 |
| 23 | 30 | 80 | 37.5 | dinonyl adipate | 22.5 | 44.1 | 1 |
| 24 | 30 | 80.2 | 37.5 | diisodecyl adipate | 23 | 59.4 | 1 |
| 25 | 30 | 79.8 | 44.4 | diisodecyl adipate | 26.7 | 75.4 | 1 |
| 26 | 30 | 79.5 | 54.4 | diisodecyl adipate | 31 | 121 | 1-2 |
| 27 | 30 | 81 | 37.5 | diisodecyl phthalate | 25.3 | 262 | 1 |
| 28 | 30 | 80.5 | 54.4 | diisodecyl phthalate | 33.6 | 500 | 1-2 |

EXAMPLES 29 TO 33

Preparation of known polar superparamagnetic liquids by the appropriate novel process;

method of preparation

Examples 22 to 25 and Example 27 were repeated, known superparamagnetic solid particles (mixed phase of $Fe_3O_4$ and $\gamma$-$Fe_2O_3$) prepared from 197.1 g of $FeCl_3.6H_2O$ and 103.4 g of $FeCl_2.2H_2O$ being used instead of the solid particles I.

Table 11 provides information on the type and amount of substances used, the yield of solid particles and the measured values obtained for the polar superparamagnetic liquids.

The Examples in Table 11 can be compared directly with those in Table 10, as follows: 29 with 22, 30 with 23, 31 with 24, 32 with 25 and 33 with 27.

The comparison again shows that the novel solid particles I have particular advantages over the known ones.

On the other hand, Experiments 29 to 33 demonstrate that the novel process also gives polar superparamagnetic liquids having good performance characteristics when it is used to produce known solid particles.

TABLE 11

EXAMPLES 29 TO 33: SUBSTANCES AND TEST RESULTS

| Example no. | Acidic phosphate (g) | Yield of solid particles I in the polar liquid 1 (%) | Known polar superparamagnetic liquid % by weight of solid particles I | Known polar superparamagnetic liquid Polar liquid 2 | Saturation magnetization ($nTm^3/g$) | Viscosity at 20° C. (mPa.s) | Stability (Rating) |
|---|---|---|---|---|---|---|---|
| 29 | 20 | 66 | 37.5 | diisodecyl phthalate | 23 | — | 1 |
| 30 | 30 | 33 | 37.5 | dinonyl adipate | 16 | 57 | 1 |
| 31 | 30 | 35 | 37.5 | diisodecyl adipate | 17.7 | 75 | 1 |
| 32 | 30 | 34 | 44.4 | diisodecyl adipate | 20 | 99 | 2 |
| 33 | 30 | 36 | 37.5 | diisodecyl phthalate | 19.6 | 348 | 1-2 |

COMPARATIVE EXPERIMENT K

Preparation of a known polar superparamagnetic liquid by a prior art process (U.S. Pat. No. 4,430,239);

method of preparation

About 100 g of superparamagnetic magnetite were prepared and dispersed in 313 g of the acidic monoester of phosphoric acid with oxyethylated (p=3-5) ω-phenylnonyl alcohol and 3130 ml of water, these steps being carried out according to the method described in Example 1 of U.S. Pat. No. 4,430,239.

3000 ml of acetone were added to this dispersion, with the result that the coated superparamagnetic magnetite particles were flocculated. The flocculated particles were isolated from the water/acetone mixture and washed with 6000 ml of acetone.

The washed, moist particles were redispersed in 250 ml of di-(2-ethylhexyl) azelaate, after which residual water and acetone were distilled off.

A polar superparamagnetic liquid containing 33% by weight of superparamagnetic solid particles resulted. It had a saturation magnetization of 39 $nTm^3/g$ and a viscosity of 140 mPa.s at 20° C. However, it contained even larger amounts of solid particles capable of sedimentation. These were removed by centrifuging, with the result that the amount of superparamagnetic solid particles in the polar superparamagnetic liquid decreased to 23.5% by weight. However, this less concentrated superparamagnetic liquid was also unstable and exhibited marked sedimentation (rating 3 to 4).

We claim:

1. Superparamagnetic cubic ferrite particles of the formula $$M_v Mn_w Zn_x Fe_y O_z \quad (I)$$

where M is selected from the group consisting of Co and Ni, v and w are each from 0 to 0.998, x is from 0.001 to 0.998, y is from 2.001 to 2.998, z is from 3.001 to 4, v+w+x is from 0.001 to 0.999, v+w+x+y is 3, v≠0 if w=0, and w≠0 if v=0; having a BET inner surface area of from 40 to 130 $m^2/g$ and a saturation magnetization $M_s$ of larger than 60 $nTm^3/g$ in a magnetic field of 160 kA/m, said particles displaying a hysteresis-free reversible magnetization and demagnetization behavior when dispersed colloidally in a liquid.

2. The superparamagnetic cubic ferrite particles of claim 1, having a BET inner surface area of from 50 to 120 $m^2/g$.

3. The superparamagnetic cubic ferrite particles of claim 1, having a BET inner surface area of from 60 to 110 $m^2/g$.

4. The superparamagnetic cubic ferrite particles of claim 1, having a maximum particle diameter of from about 5 to 15 nm.

* * * * *